US011132815B2

(12) United States Patent
Tu et al.

(10) Patent No.: US 11,132,815 B2
(45) Date of Patent: Sep. 28, 2021

(54) METHOD AND SYSTEM FOR INDEXING BLOOD VESSEL CORRESPONDING POSITIONAL RELATIONS IN MULTI-ANGLE ANGIOGRAPHY

(71) Applicant: Shanghai Jiaotong University, Shanghai (CN)

(72) Inventors: Shengxian Tu, Shanghai (CN); Lulu Yang, Shanghai (CN); Junqing Yang, Shanghai (CN); Su Zhang, Shanghai (CN)

(73) Assignee: Shanghai Jiaotong University, Shanghai (CN)

( * ) Notice: Subject to any disclaimer, the term of this patent is extended or adjusted under 35 U.S.C. 154(b) by 52 days.

(21) Appl. No.: 16/618,552

(22) PCT Filed: May 29, 2018

(86) PCT No.: PCT/CN2018/088858
§ 371 (c)(1),
(2) Date: Jan. 27, 2020

(87) PCT Pub. No.: WO2018/219273
PCT Pub. Date: Dec. 6, 2018

(65) Prior Publication Data
US 2020/0388050 A1    Dec. 10, 2020

(30) Foreign Application Priority Data

Jun. 1, 2017  (CN) .......................... 201710404200.7

(51) Int. Cl.
*G06K 9/00* (2006.01)
*G06T 7/73* (2017.01)
*A61B 6/00* (2006.01)

(52) U.S. Cl.
CPC ............... *G06T 7/74* (2017.01); *A61B 6/504* (2013.01); *A61B 6/5217* (2013.01); *A61B 6/582* (2013.01); *G06T 2207/30101* (2013.01)

(58) Field of Classification Search
CPC ....................................................... G06T 7/74
See application file for complete search history.

(56) References Cited

U.S. PATENT DOCUMENTS 6,381,302 B1  4/2002  Berestov
7,180,976 B2  2/2007  Wink et al.
(Continued)

FOREIGN PATENT DOCUMENTS

CN    1700885 A    11/2005
CN    101283910 A    10/2008
(Continued)

*Primary Examiner* — Oneal R Mistry
(74) *Attorney, Agent, or Firm* — Elmore Patent Law Group, P.C.; Carolyn S. Elmore; Joseph C. Zucchero

(57) ABSTRACT

A system and method for retrieving a blood vessel corresponding positional relation under multi-angle angiography. The system includes an angiography machine, an angiographic image receiving module, a center point calibration module, a corresponding feature point detection module, and a feature point corresponding blood vessel module. The angiography machine is used for performing angiography and collecting angiographic images of multiple projection body positions. The angiographic image receiving module is used for receiving an angiographic image and transmitting the angiographic image to the center point calibration module. The center point calibration module is used for calibrating a center point offset caused by the multi-angle angiography system and transmitting the result to the feature point detection module. The feature point detection module receives several feature points of a target blood vessel of a reference projection angle angiographic image and detects corresponding feature points of a second projection angle (Continued)

angiographic image via a spatial epipolar constraint relationship. The feature point corresponding blood vessel module is used for determining a blood vessel on which the feature points are located. The system simplifies complexity of detection on corresponding relationship, and ensures accuracy of the result while implementing noninvasive detection.

12 Claims, 4 Drawing Sheets

(56) References Cited

U.S. PATENT DOCUMENTS

| | | | |
|---|---|---|---|
| 2005/0200624 A1 | 9/2005 | Lachner et al. | |
| 2007/0116342 A1* | 5/2007 | Zarkh | G06T 7/564 382/130 |
| 2008/0009716 A1* | 1/2008 | Ohishi | G06T 7/73 600/425 |
| 2015/0351713 A1* | 12/2015 | Sato | A61B 6/504 378/41 |
| 2016/0078620 A1* | 3/2016 | Iwanaka | A61B 6/504 600/424 |

FOREIGN PATENT DOCUMENTS

| | | |
|---|---|---|
| CN | 101283911 A | 10/2008 |
| CN | 107233106 A | 10/2017 |
| JP | 5121173 B2 | 11/2012 |
| WO | 2005020155 A1 | 3/2005 |

\* cited by examiner

METHOD AND SYSTEM FOR INDEXING BLOOD VESSEL CORRESPONDING POSITIONAL RELATIONS IN MULTI-ANGLE ANGIOGRAPHY

TECHNICAL FIELD

The present invention relates to an image data processing system for blood vessel angiography and a convenient retrieval system applied to determining a corresponding blood vessel positional relation under multi-angle angiography, includes an epipolar constraint relationship of angiographic images of multiple projection angles and detection of a corresponding position feature point, and in particular, relates to determining a corresponding relationship of a blood vessel with large morphological differences at different angiography angles, or multiple blood vessels with rather similar morphology.

BACKGROUND

To make a blood vessel angiographic image more truly reflect a distribution structure of blood vessels, the current clinical angiography system often performs multi-angle X-ray angiography on the blood vessels, and a true structure of the blood vessels is determined by clinician's inspection of a corresponding relationship of the multi-angle angiographic images. However, when the blood vessels are greatly different in morphology, or when there are multiple blood vessels with similar morphology, it is sometimes difficult to confirm a positional relation of the same blood vessel in angiographic images of two projection angles.

In addition, currently, in the prior art, percutaneous intervention can be performed on a blood vessel by using a guide wire, and a corresponding blood vessel can be determined according to a position of the guide wire in the multi-angle angiographic images. Although this method can implement confirming of the corresponding blood vessel in the multi-angle angiographic images, percutaneous intervention with guidewires is required, there is a high risk of trauma due to complicated operations, and it takes a long time to complete the operations. Consequently, the results cannot be obtained quickly, and the use of guidewires also leads to rise of costs.

SUMMARY

In view of this, embodiments of the present invention provide a method and a system for retrieving a blood vessel corresponding positional relation under multi-angle angiography, and a blood vessel corresponding relationship in images of two angiography angles by using an epipolar constraint relationship of two angiographic surfaces. To achieve the above object, the present invention specifically provides the following technical solution:

According to an aspect, the present invention provides a system for retrieving a blood vessel positional relation under multi-angle angiography. The system includes an angiography machine, an angiographic image receiving module, a center point calibration module, a feature point detection module, a feature point corresponding blood vessel module.

The angiography machine is used for: blood vessel angiography at multiple projection angles, and collection of an angiographic image.

The angiographic image receiving module is used for: receiving the image from the angiography machine, and transmitting the image to the center point calibration module.

The center point calibration module is used for calibrating a center point offset caused by looseness and rotation of a mechanical arm of the multi-angle angiography system.

The feature point detection module is used for: receiving several feature points of a target blood vessel on a reference image inputted by a display module, and detecting corresponding feature points on a second image via a spatial epipolar constraint relationship.

The feature point corresponding blood vessel module is used for determining a blood vessel on which the feature points are located. The feature point refers to an anatomical landmark point capable of representing a blood vessel morphological feature.

Preferably, the center point calibration module further includes:

a calibration point input module, used for receiving several pairs of corresponding position feature points of user-inputted angiographic images of two projection angles; an epipolar constraint module, used for calculating an epipolar line of a reference image projection point on the second image via the epipolar constraint relationship; an error minimization module, used for: using a first projection system as a fixed system, comprehensively define a sum of distances between projection points of several calibration points on the second image and corresponding epipolar lines as an error function, and adjusting the epipolar constraint relationship by using the error function to calibrate a position of a center point of a second projection system; and a center point transformation module, used for transforming the spatial position of the center point of the second angiography angle, to reduce an offset error of the center points at the two angiography angles. The center point is the center of rotation of a C-arm in the angiography machine, or the center of a framing space when another angiography device performs angiography.

Preferably, the feature point detection module further includes:

a reference image feature point input module, used for manually selecting several feature points of the reference image target blood vessel; an epipolar constraint module, used for calculating an epipolar position of the reference image feature point on the second image by using the spatial epipolar constraint relationship; and a second image feature point corresponding position obtaining module, used for determining a corresponding position of the reference image feature points on the second image by using intersection positions of several epipolar lines and the blood vessel in the second image.

Preferably, the center points of the two angiography angles are calibrated by using the epipolar constraint relationship to avoid a search error.

Preferably, the corresponding position of the target blood vessel feature point of the reference angle angiographic image on the second angle image is searched for by using a spatial constraint relationship obtained after center point offset calibration.

Preferably, several feature points are set on the target blood vessel segment, and a corresponding positional relation of a blood vessel on which the feature points are located is determined by a positional relation of the feature points on angiographic images of two angles.

Preferably, the system further includes a display module, used for: inputting the feature points by using human-computer interaction, and displaying a detection result of the feature points of the corresponding position.

According to another aspect, the present invention further provides a method for retrieving a blood vessel corresponding positional relation under multi-angle angiography. The method can be implemented by using the system as described above, and the method includes:

Step 1: receiving and storing angiographic images of at least two projection angles;

Step 2: selecting a corresponding anatomical point in the angiographic images of at least two projection angles as a calibration point, and performing center point calibration on the angiographic images of at least two projection angles; and Step 3: For the angiographic images of at least two projection angles after center point calibration, selecting a feature point of a target blood vessel on a reference image, calculating an epipolar line of the feature point on the other image, and determining a position of the target blood vessel in the other image by using an intersection point of the epipolar line and the blood vessel.

Preferably, in Step 3, the epipolar line of the reference image feature point on the second image is calculated by using the spatial epipolar constraint relationship.

Preferably, the feature point is located at an intersection point of a main blood vessel and a side branch blood vessel.

Preferably, the method and system are particularly applicable to determining the corresponding positional relation of a same blood vessel in images of different angiography angles when the blood vessel has large morphological differences at different angiography angles, or there are multiple blood vessels with similar morphology.

Compared with the prior art, the technical solution of the present invention simplifies complexity of direct correspondence detection on a blood vessel in the prior art; and performs corresponding feature point detection on angiographic images of at least two angles based on a spatial constraint relationship, so that accuracy of the test results is guaranteed while noninvasive detection is implemented.

BRIEF DESCRIPTION OF DRAWINGS

In order to more clearly explain the embodiments of the present invention or the technical solutions in the prior art, the drawings used in the description of the embodiments or the prior art will be briefly introduced below. Obviously, the drawings in the following description are merely some embodiments of the present invention. For a person of ordinary skill in the art, other drawings can be obtained according to these drawings without creative efforts.

DETAILED DESCRIPTION OF EMBODIMENTS

The following describes the technical solutions in the embodiments of the present invention in detail with reference to the accompanying drawings in the embodiments of the present invention. It should be clear that the described embodiments are merely some but not all of the embodiments of the present invention. All other embodiments obtained by a person of ordinary skill in the art based on the embodiments of the present invention without creative efforts shall fall within the protection scope of the present invention.

The person skilled in the art should know that the following specific embodiments or specific implementations are a series of optimized setting manners enumerated in the present invention to further explain the specific content of the present invention, and these setting manners can be combined with each other or can be used in association with each other, unless it is explicitly proposed in the present invention that some embodiments or implementations or a specific embodiment or implementation cannot be associated with or used with other embodiments or implementations. At the same time, the following specific examples or implementations are only used as optimal setting manners, but not as an understanding to limit the protection scope of the present invention.

Embodiment 1

Figure 1:
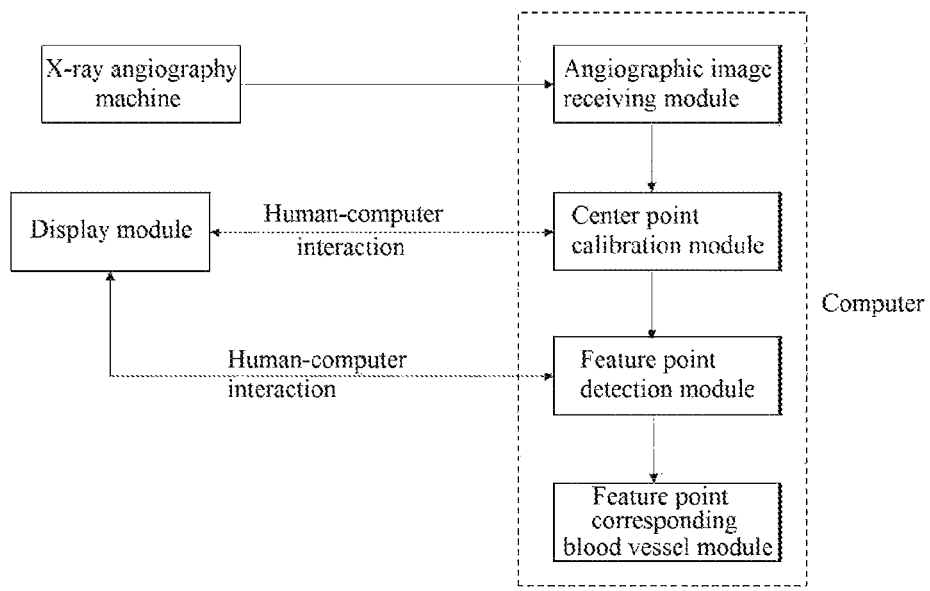
FIG. 1 is a schematic diagram of a system for retrieving a blood vessel corresponding positional relation under multi-angle angiography.

As shown in FIG. 1, the present invention provides a system for retrieving a blood vessel corresponding positional relation under multi-angle angiography. The system includes an angiography machine, an angiographic image obtaining module, a center point calibration module, a feature point detection module, a feature point corresponding blood vessel module, and a display module. The angiography machine may be a possible angiography device, for example, an X-ray angiography machine, and a CT.

The angiography machine is used for performing multi-angle angiography on a blood vessel. The angiographic image receiving module is used for: receiving angiographic images of multiple projection angles and transmitting the images to the center point calibration module. It should be emphasized that the multi-angle angiography herein can be performed at two angles, three angles, or even more angles. When more angles are selected, retrieval accuracy is higher. When more angles are selected, the same center point calibration method and corresponding algorithm of the feature points are used. For example, one angiographic image can still be selected as a reference image to calculate a corresponding epipolar line of the remaining one or more images. In subsequent specific embodiments, performing angiography at only two angles is used as an example, but should not be understood as the limitation of the protection scope of the present invention. The center point calibration module includes a calibration point input module, an epipolar constraint module, an error minimization module, and a center point transformation module, to reduce a center point offset existing in the multi-angle angiography, and transmit the calibrated image to the corresponding feature point detection module. The corresponding feature point detection module is used for detecting corresponding feature points of reference image input feature points on a second image. The feature point corresponding blood vessel module receives second-angle image feature points outputted by the feature point detection module, and confirms a blood vessel on which the corresponding feature points on the second image are located. The display module is used for performing inputting of manually selected calibration points and outputting of search results by using human-computer interaction.

Figure 2:
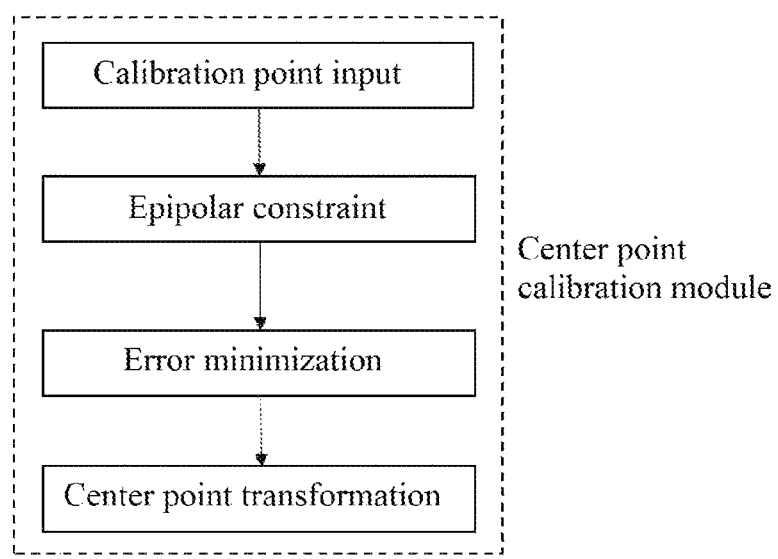
FIG. 2 is a schematic diagram of a center point calibration module.

The center point calibration module is used for reducing the center point offset existing in the multi-angle angiography. As shown in FIG. 2, the calibration point input module is used for receiving several corresponding position projection points selected by a user on images of two angiography angles. The epipolar constraint module is used for calculating epipolar lines corresponding to the two projection points. The error minimization module defines a sum of distances between the projection points and the epipolar lines in the two projection planes as an error function, and obtains a value of the error function. The center point transformation module transforms a physical position of a center point of the second angiography angle based on the calculation result of the error minimization module, to calibrate a center point offset error of the two angiography angles.

Figure 3:
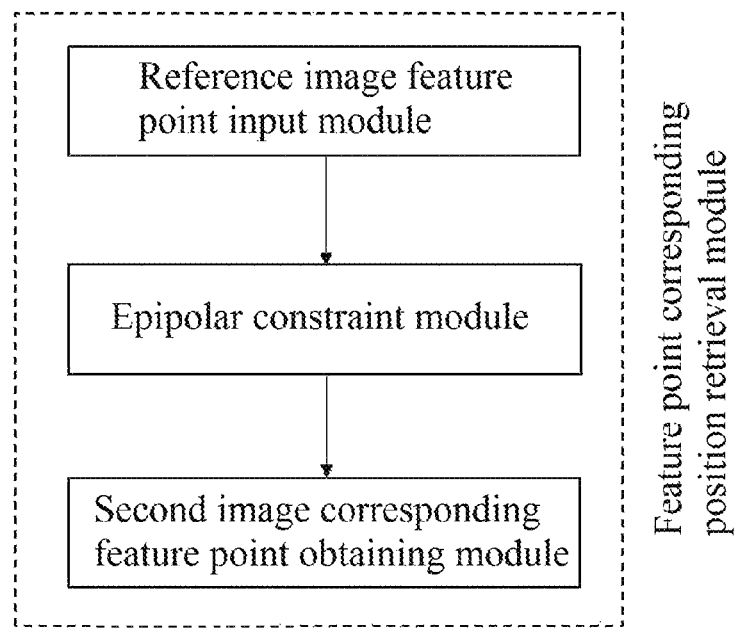
FIG. 3 is a schematic diagram of a feature point detection module.

The feature point detection module is used for detecting a corresponding position of the reference image feature point on the second image. As shown in FIG. 3, the reference image feature point input module is used for manually selecting several feature points of a reference image target blood vessel. The epipolar constraint module calculates an epipolar position of the reference image feature point on the second image by using a spatial epipolar constraint relationship. The second image feature point corresponding position obtaining module determines corresponding positions of the reference image feature points on the second image by using intersection points of several epipolar lines and the blood vessel in the second image.

Embodiment 2

Figure 4:
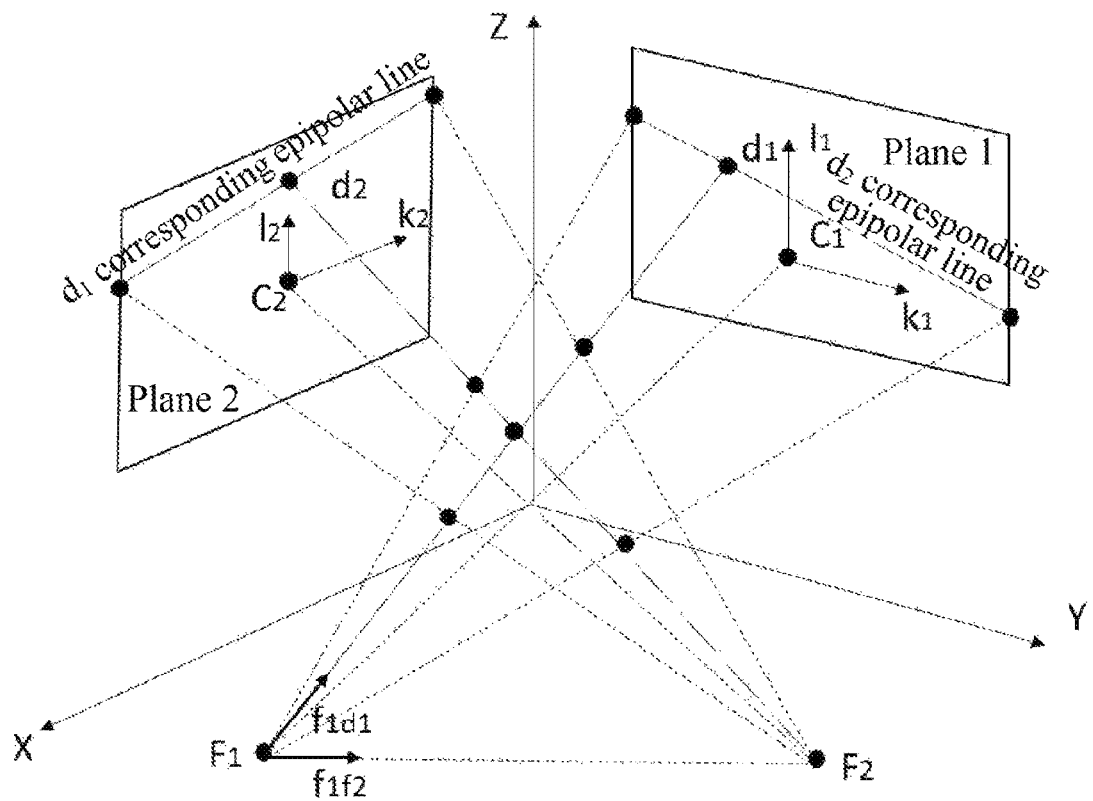
FIG. 4 is a schematic diagram of a spatial coordinate system and an epipolar constraint relationship of a dual projection system.

In a specific embodiment, referring to FIG. 4, the epipolar constraint relationship in the present invention is further explained. It should be noted that various epipolar constraint relationships can be used, such as a spatial offset algorithm in the prior art. The following embodiment is only used as a preferred embodiment, to further explain the principle of the present invention, but should not be understood as a limit of the protection scope of the present invention.

An epipolar constraint relationship of spatial points on two projection planes is shown in FIG. 4. A projection point of a point d in space on a first projection plane is $d_1$, and a projection line $l_1$ of a connection line of d and $d_1$ on a second projection plane is defined as an epipolar line of $d_1$ on the second projection plane, and a projection line $l_2$ of a connection line of d and $d_2$ on the first projection plane is defined as an epipolar line of $d_2$ on the first projection plane. When the center points in the two projection angles coincide, $d_1$ must be located on the projection line $l_2$, and $d_2$ must be located on the projection line $l_1$. This spatial correspondence is referred to as epipolar constraint.

As shown in FIG. 4, in a space coordinate system of a dual projection system, an origin of the coordinate system is a center point of the projection system. A ray source of the first projection system is $F_1$, $f_1d_1$ is a unit vector from the ray source to $d_1$, a ray source of a second projection system is $F_2$, $f_2d_2$ is a unit vector from the ray source to $d_2$, and $C_1$ and $C_2$ are projection points of the center point of the projection system on the two projection planes. Assuming that spatial coordinate of d is x(x,y,z), then for x:

$$[r_u, r_v, r_w]^T = P[x,y,z,l]^T,$$

Wherein a pixel position of this point on the first projection plane is $(x_1, y_1) = (r_u/r_w, r_v/r_w)$, the projection matrix P is calculated by a stereo theory, and an expression is as follows:

$$P = \begin{bmatrix} -SID \cdot U/IS & 0 & U/2 \\ 0 & SID \cdot V/IS & V/2 \\ 0 & 0 & 1 \end{bmatrix} \begin{bmatrix} \ddots & 0 & 0 & 0 \\ 0 & R_{PA} \cdot R_{SA} & 0 & 0 \\ 0 & 0 & \ddots & -SOD \end{bmatrix},$$

Wherein, $$R_{PA} = \begin{bmatrix} \cos\theta & 0 & -\sin\theta \\ 0 & 1 & 0 \\ \sin\theta & 0 & \cos\theta \end{bmatrix}, R_{SA} = \begin{bmatrix} \cos\varphi & \sin\varphi & 0 \\ -\sin\varphi & \cos\varphi & 0 \\ 0 & 0 & 1 \end{bmatrix}$$

U, V: a pixel dimension of an image
IS: an actual length of the image in the U or V direction
SID: a distance between an X-ray source and an image intensifier
SOD: a distance between an X-ray source and a projected object
θ: a first angle (left front oblique/right front oblique, left front oblique is positive, the first projection system)
ψ: a second angle (head position/foot position, head position is positive, the first projection system)

According to the pixel position $(x_1, y_1)$ of this point on the first projection plane, the true coordinate position of this point on the projection surface is calculated: $x_k = k_1 \cdot x$, $y_1 = l_1 \cdot y$, and $k_1$, $l_1$ are two coordinate vectors of the projection plane; then the corresponding epipolar line of the projection point of the first projection plane on the second projection plane is $y_1(x_k)$ and meets the following equation:

$$vf_1f_2 + \mu f_1 d_1 + F_1 = x_k k_2 + y_1 l_2 + C_2,$$

wherein, $f_1f_2$ is a unit vector from the ray source of the first projection system to the ray source of the second projection system.

Similarly, the projection point $d_2$ of the second projection system and the corresponding epipolar line can be calculated.

Embodiment 3

Figure 5:
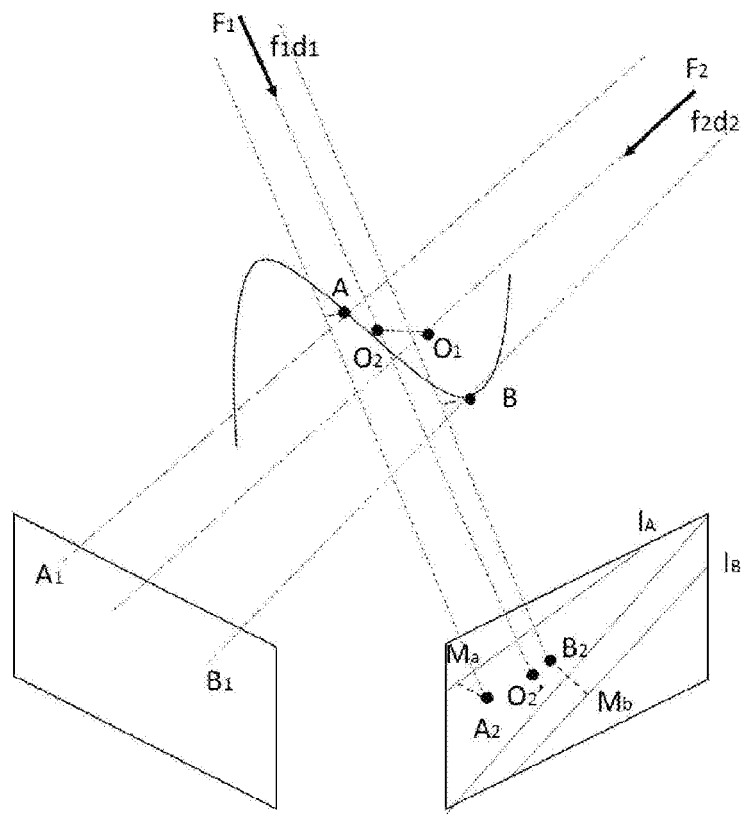
FIG. 5 is a schematic diagram of a center point offset of a dual projection system.

This embodiment is used to describe a specific method for center point offset calibration. This method is only used as an example of a specific available embodiment, and a specific calculation manner of the method should not be understood as the limited scope of the present invention. In a specific implementation, for example, images of two angles are used as an example. When there is an offset of the center points in the two projection angles, the system does not meet the epipolar constraint relationship, and the projection point has a corresponding offset from the projection line. As shown in FIG. 5, there is a center point offset $(o_1 - o_2)$ in the first projection system and the second projection system of the dual projection system, and there is an offset between projection points $A_2$ and $B_2$ of calibration points A and B on the second image and epipolar lines $l_A$ and $l_B$ corresponding to projection points $A_1$ and $B_1$ on the first image in FIG. 5. When the system detects that the offset is not zero, that is, when the error function is not zero, the first projection system is used as a fixed system, and center point offset calibration is performed on the second projection system.

As shown in FIG. 5, a ray source of the first projection system is $F_1$, $f_1 o_1$ is a unit vector from the ray source to the center point projection point $o_1$, a ray source of the second projection system is $F_2$, and $f_2 o_2$ is a unit vector from the ray source to the center point projection point $o_2$; then vectors of the two projection lines respectively are:

$$F_1 + \tau f_1 o_1$$

and $$F_2 \pm \sigma f_2 o_2.$$

Validated by space theory, in this case, when the center point o of the second projection system after calibration is located on the common vertical line of the two projection lines, the error function defined by the error minimization module has the smallest value, and then the vector s of the straight line where this point is located meets the equation:

$$s = (F_1 + \tau f_1 o_1) - (F_2 + \sigma f_2 o_2).$$

Restriction conditions are as follows:
$s f_1 o_1 = 0$,
$s f_2 o_2 = 0$.
By solving the above equation, the followings are obtained:

$$\frac{f_2 o_2 \cdot (f_1 - f_2) * f_1 o_1 \cdot f_1 o_1 - f_1 o_1 \cdot (f_1 - f_2) * f_1 o_1 \cdot f_1 o_2}{f_1 o_1 \cdot f_1 o_1 * f_2 o_2 \cdot f_2 o_2 - (f_1 o_1 \cdot f_2 o_2)^2} \text{ and}$$

$$\tau = \frac{\sigma f_1 o_1 \cdot f_2 o_2 - f_1 o_1 \cdot (f_1 - f_2)}{f_1 o_1 \cdot f_1 o_1}$$

Then the position of the point o is as follows:

$$o = F_1 + \tau f_1 o_1 + \tfrac{1}{2} s,$$

That is, the position of the center point of the second projection system after calibration.

Embodiment 4

Figure 6A:
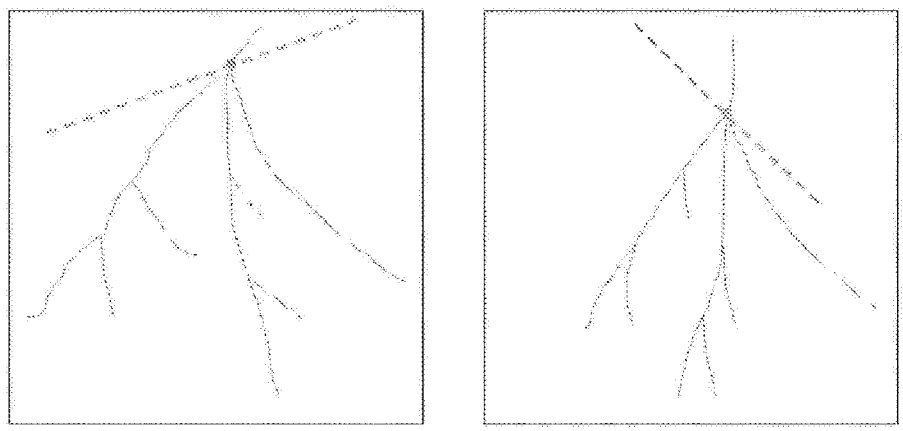
FIG. 6a is a schematic diagram of a blood vessel corresponding positional relation under the multi-angle angiography for multiple morphologically similar blood vessels before a center point selected by the user is calibrated.
Figure 6B:
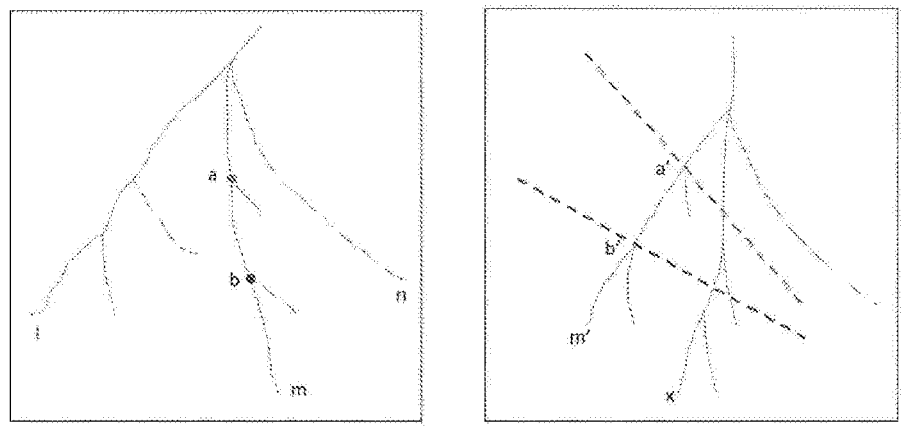
FIG. 6b is a schematic diagram of a blood vessel corresponding positional relation under multi-angle angiography for multiple morphologically similar blood vessels after the center point is calibrated.

In yet another specific embodiment, the present invention discloses a retrieval method for determining a blood vessel correspondence positional relation under multi-angle angiography. The method includes the following steps:

During working, firstly, angiographic images of two projection angles are received from an angiography machine and stored in a computer. Secondly, as shown in FIG. 6a, a user selects corresponding anatomical points in the two images as calibration points via a display module, and uses a center point calibration module to perform center point calibration on multi-angle angiography. Thirdly, as shown in FIG. 6b, for the two images after center point calibration, the user selects two points a and b (an intersection point of a main blood vessel and a side branch blood vessel) of a target blood vessel on the reference projection angle angiographic image as feature points, and the computer calculates epipolar lines of the points on the second image by using a spatial epipolar constraint relationship (the constraint relationship and the calculation method may use, for example, the method described in Embodiment 2). The blood vessels l and m in FIG. 6a have very similar morphological features, and it is difficult for naked eyes to determine the correspondence between the blood vessels l and m and the blood vessels in FIG. 6b. When this method is used, two epipolar lines on the second image of points a and b intersect the blood vessel m' at bifurcation points of the blood vessel. Therefore, m and m' correspond to the same blood vessel in space. However, there is no bifurcation blood vessel at intersection points of the epipolar lines and the blood vessel x. Therefore, the intersection points are not the corresponding positions of the reference image feature points on the second image, that is, in and x correspond to different blood vessels in space. Note: The projection point in FIG. 6 and the corresponding epipolar line have the same color.

Figure 7A:
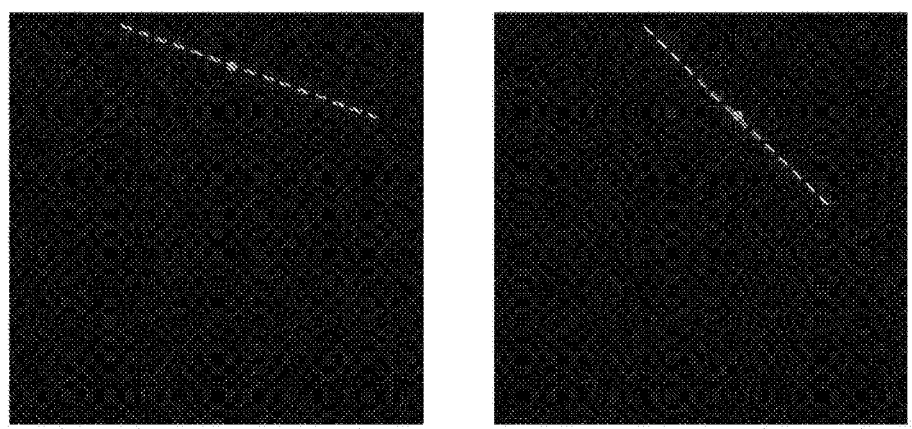
FIG. 7a is a schematic diagram of a blood vessel corresponding positional relation under multi-angle angiography for a blood vessel with large morphological differences before the center point offset is calibrated.
Figure 7B:
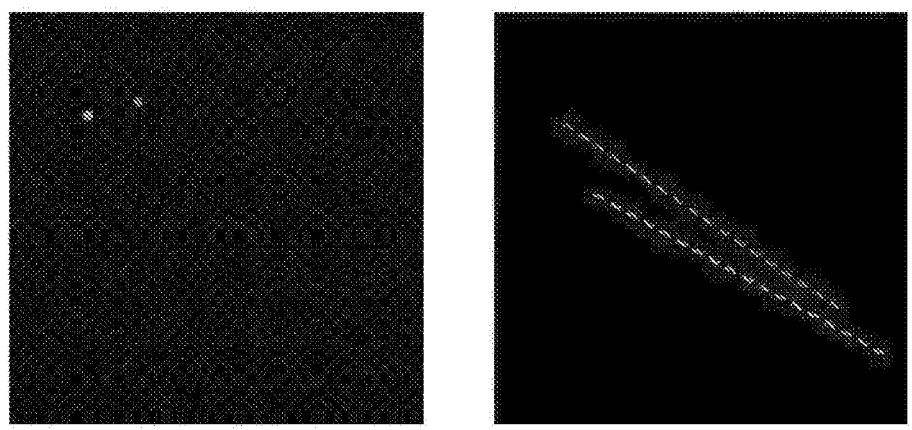
FIG. 7b is a schematic diagram of a blood vessel corresponding positional relation under multi-angle angiography for a blood vessel with large morphological differences after the center point offset is calibrate.

Similarly, FIG. 7a is a schematic diagram of center point offset calibration of another two images. Blood vessels l and l' in FIG. 7 are angiographic images of a blood vessel in space at different angles, but have large morphological differences. Therefore, it is difficult for naked eyes to directly determine whether the blood vessels l and l' correspond to the same blood vessel. When this method is used, the two epipolar lines on the second image of points a and b intersect the blood vessel l' at bifurcation points of the blood vessel, and there is no bifurcation blood vessel at intersection points of the epipolar lines and the blood vessel x. Therefore, it can be confirmed that l and l' correspond to the same blood vessel in space.

Preferably, the system and method are particularly applicable to the situations shown in FIGS. 6 and 7: Multiple blood vessels with very similar morphology or a position correspondence of a blood vessel with large morphology differences under angiography of different angles are determined by specifying vascular anatomical points with obvious characteristics, so that higher accuracy can be obtained compared with naked eye observation.

One of innovations of the present invention is to set several feature points on a target blood vessel of an angiographic image, and a corresponding relationship of the blood vessel on which the feature points are located is determined based on the correspondence between the feature points of the images of two angiography angles, so that complexity of direct detection on the blood vessel corresponding relationship is simplified; Detection on corresponding feature points is performed on the images of two angiography angles based on the spatial constraint relationship, so that accuracy of the detection result is ensured while non-invasive detection is implemented.

The person of ordinary skill in the art can understand that all or some of the processes in the method of the foregoing embodiment can be implemented by using a computer program to instruct related hardware. The program can be stored in a computer-readable storage medium. When the program is executed, the processes of the embodiments of the methods described above may be included. The storage medium may be a magnetic disk, an optical disk, a Read-Only Memory (ROM), or a Random Access Memory (RAM).

The foregoing descriptions are merely specific implementations of the present invention, but are not intended to limit the protection scope of the present invention. Any variation or replacement readily figured out by a person skilled in the art within the technical scope disclosed in the present invention shall fall within the protection scope of the present invention. Therefore, the protection scope of the present invention shall be subject to the protection scope of the claims.

The invention claimed is:

1. A system for retrieving a blood vessel corresponding positional relation under multi-angle angiography, wherein the system comprises an angiography machine, an angiographic image receiving module, a center point calibration module, a feature point detection module, and a feature point corresponding blood vessel module, wherein the angiography machine is use for blood vessel angiography at multiple projection angles, and collection of an angiographic image;

the angiographic image receiving module is used for: receiving the image from the angiography machine, and transmitting the image to the center point calibration module;

the center point calibration module is used for calibrating a center point offset caused by looseness and rotation of a mechanical arm of the multi-angle angiography system;

the feature point detection module is used for: receiving several feature points of a target blood vessel on a reference image inputted by a display module, and detecting corresponding feature points on a second image via a spatial epipolar constraint relationship;

the feature point corresponding blood vessel module is used for determining a blood vessel on which the feature points are located, wherein the feature point refers to an anatomical landmark point capable of representing a blood vessel morphological feature, and wherein the center point calibration module further comprises:

a calibration point input module, used for receiving several pairs of corresponding position feature points of user-inputted angiographic images of two projection angles;

an epipolar constraint module, used for calculating an epipolar line of a reference image projection point on the second image via the epipolar constraint relationship;

an error minimization module, used for: defining an error as a sum of distances between several pairs of corresponding projection points inputted by the calibration point input module and corresponding epipolar lines, and adjusting the epipolar constraint relationship by using an error function to calibrate a center point; and a center point transformation module, used for transforming a spatial position of a center point of a second angiography angle, to reduce an offset error of the center points of two angiography angles.

2. The system according to claim 1, wherein the feature point detection module further comprises:

a reference image feature point input module, used for manually selecting several feature points of the reference image target blood vessel;

the epipolar constraint module, used for calculating an epipolar position of the reference image feature points on the second image by using the spatial epipolar constraint relationship; and a second image feature point corresponding position obtaining module, used for determining a corresponding position of the reference image feature points on the second image by using intersection positions of several epipolar lines and the blood vessel on the second image.

3. The system according to claim 2, wherein the center points of two angiography angles are calibrated by using the epipolar constraint relationship to avoid a search error.

4. The system according to claim 2, wherein the corresponding position of the target blood vessel feature point of the reference angle angiographic image on the second angle image is searched for by using a spatial constraint relationship obtained after center point offset calibration.

5. The system according to claim 2, wherein several feature points are set on the target blood vessel segment, and a corresponding positional relation of a blood vessel on which the feature points are located is determined by a positional relation of the feature points in angiographic images of two angles.

6. The system according to claim 1, wherein the center points of two angiography angles are calibrated by using the epipolar constraint relationship to avoid a search error.

7. The system according to claim 1, wherein the corresponding position of the target blood vessel feature point of the reference angle angiographic image on the second angle image is searched for by using a spatial constraint relationship obtained after center point offset calibration.

8. The system according to claim 1, wherein several feature points are set on the target blood vessel segment, and a corresponding positional relation of a blood vessel on which the feature points are located is determined by a positional relation of the feature points in angiographic images of two angles.

9. The system according to claim 1, wherein the system further comprises a display module, used for inputting the feature points by using human-computer interaction, and displaying a detection result of corresponding position feature points.

10. A method for retrieving a blood vessel corresponding positional relation under multi-angle angiography, wherein the method comprises:

Step 1: receiving angiographic images of at least two projection angles comprising receiving feature points of a target blood vessel on a reference image, detecting corresponding feature points on at least one further image via a spatial epipolar constraint relationship; determining a blood vessel on which the feature points are located, wherein the feature point refers to an anatomical landmark point capable of representing a blood vessel morphological feature; and storing the angiographic images;

Step 2: selecting a corresponding anatomical point in the angiographic images of at least two projection angles as a calibration point, and performing center point calibration on the angiographic images of at least two projection angles; and Step 3: for the angiographic images of at least two projection angles after center point calibration, selecting a feature point of a target blood vessel on a reference image, calculating an epipolar line of the feature point on the other image, and determining a position of the target blood vessel in the other image by using an intersection point of the epipolar line and the blood vessel.

11. The method according to claim 10, wherein in Step 3, the epipolar line of the reference image feature point on the second image is calculated by using a spatial epipolar constraint relationship.

12. The method according to claim 10, wherein the feature point is located at an intersection point of a main blood vessel and a side branch blood vessel.

* * * * *